US008755877B2

(12) United States Patent
Zoica

(10) Patent No.: US 8,755,877 B2
(45) Date of Patent: Jun. 17, 2014

(54) REAL TIME QRS DETECTION USING ADAPTIVE THRESHOLD

(75) Inventor: Vasile Zoica, La Gaude (FR)

(73) Assignee: Texas Instruments Incoporated, Dallas, TX (US)

( * ) Notice: Subject to any disclaimer, the term of this patent is extended or adjusted under 35 U.S.C. 154(b) by 105 days.

(21) Appl. No.: 13/434,725

(22) Filed: Mar. 29, 2012

(65) Prior Publication Data

US 2013/0237874 A1    Sep. 12, 2013

(30) Foreign Application Priority Data

Mar. 12, 2012 (EP) .................................... 12290088

(51) Int. Cl.
*A61B 5/0456* (2006.01)
(52) U.S. Cl.
USPC ............................ 600/521; 600/509; 600/517
(58) Field of Classification Search
USPC .......................................... 600/509, 521, 517
See application file for complete search history.

(56) References Cited

U.S. PATENT DOCUMENTS

| 7,383,079 | B2 * | 6/2008 | Holland ........................ 600/509 |
| 2003/0187479 | A1 | 10/2003 | Thong |
| 2005/0049515 | A1 | 3/2005 | Misczynski et al. |
| 2009/0062671 | A1 | 3/2009 | Brockway et al. |
| 2009/0171227 | A1 * | 7/2009 | Dziubinski et al. ............ 600/516 |
| 2010/0160797 | A1 | 6/2010 | Banet et al. |

FOREIGN PATENT DOCUMENTS

WO    WO 2011115579    9/2011

OTHER PUBLICATIONS

"Low-Power, 8-Channel, 24-Bit Analog Front-End for Biopotential Measurements", SBAS459I, Texas Instruments Incorporated, Jan. 2010, Revised Jan. 2012, pp. 1-86.
"Texas Instruments unveils fully integrated analog front end for ECG and EEG applications", Texas Instruments Incorporated, pp. 1-2, Feb. 7, 2012, available at http://newscenter.ti.com/Blogs/newsroom/archive/2010/03/22/texas-instruments-unveils-fully-integrated-analog-front-end-for-ecg-and-eeg-applications-367251.aspx.
"Our Story", NuMetrex, p. 1, Feb. 10, 2012, available at http://www.numetrex.com/company/our-story.
Ren-Guey Lee et al, "A Novel QRS Detection Algorithm Applied to the Analysis for Heart Rate Variability of Patients with Sleep Apnea", Biomedical Engineering—Applications, Basis & Communications, vol. 17, No. 5, Oct. 2005, pp. 258-262.

(Continued)

*Primary Examiner* — Christopher D Koharski
*Assistant Examiner* — Michael Carey
(74) *Attorney, Agent, or Firm* — Alan A. R. Cooper; W. James Brady, III; Frederick J. Telecky, Jr.

(57) ABSTRACT

A mobile system for analyzing ECG data includes an analog front end module coupled to a mobile consumer device. The analog front end module is configured to collect ECG data from one or more leads and is operable to convert the analog ECG data to digital ECG data. The mobile consumer device is coupled to receive the digital ECG data, and is configured to perform QRS detection using a filter whose cutoff frequency is adapted to noise level in real time. The ECG signal is amplified non-linearly and three windowed threshold signals (D, E, J) are derived. The cutoff frequency for the QRS detection is dynamically selected as a function of the threshold signals. A sample in the amplified signal is identified to be a heart beat point only when the sample value is equal to the first threshold signal and greater than the filtered threshold signal.

14 Claims, 11 Drawing Sheets

(56) References Cited

OTHER PUBLICATIONS

Geoffrey Green, "Implementation of algorithms for QRS detection from ECG signals using TMS320C6713 processor platform", Final Report, ELG 6163—DSP Microprocessors, Software, and Applications, Mar. 31, 2006, pp. 1-10.

"Electrocardiography", Feb. 10, 2010, pp. 1-17, available at http://en.wikipedia.org/wiki/Electrocardiography.

Jack Li, "Thermal Noise Analysis in ECG Applications", SBAA185, Texas Instruments Incorporated, May 2011, pp. 1-6.

* cited by examiner

500
REAL TIME QRS DETECTION USING ADAPTIVE THRESHOLD

CLAIM OF PRIORITY UNDER 35 U.S.C. 119(a)

The present application claims priority to and incorporates by reference European Patent Application number EP12290088.9, filed Mar. 12, 2012 entitled "Real Time QRS Detection Using Adaptive Threshold".

FIELD

The embodiments of the invention generally relate to analysis of electrocardiogram signals, and in particular to the use of low cost consumer devices for this purpose.

BACKGROUND

Electrocardiography (ECG or EKG) is a transthoracic (across the thorax or chest) interpretation of the electrical activity of the heart over a period of time, as detected by electrodes attached to the outer surface of the skin and recorded by a device external to the body. The recording produced by this noninvasive procedure is termed as electrocardiogram (also ECG or EKG). An electrocardiogram (ECG) is a test that records the electrical activity of the heart.

ECG is used to measure the rate and regularity of heartbeats as well as the size and position of the chambers, the presence of any damage to the heart, and the effects of drugs or devices used to regulate the heart, such as a pacemaker.

An ECG device detects and amplifies the tiny electrical changes on the skin that are caused when the heart muscle depolarizes during each heartbeat. At rest, each heart muscle cell has a negative charge (membrane potential) across its outer wall (or cell membrane). Increasing this negative charge towards zero (via an influx of the positive ions, Na+ and Ca++) is called depolarization, which activates the mechanisms in the cell that cause it to contract. During each heartbeat a healthy heart will have an orderly progression of a wave of depolarisation that is triggered by the cells in the sinoatrial node, spreads out through the atrium, passes through "intrinsic conduction pathways" and then spreads all over the ventricles. This is detected as tiny rises and falls in the voltage between two electrodes placed either side of the heart which is displayed as a wavy line either on a screen or on paper. This display indicates the overall rhythm of the heart and weaknesses in different parts of the heart muscle.

Usually, more than two electrodes are used and they can be combined into a number of pairs, for example: Left arm (LA), right arm (RA) and left leg (LL) electrodes form the three pairs LA+RA, LA+LL, and RA+LL. The output from each pair is known as a lead. Each lead is said to look at the heart from a different angle. Different types of EKGs can be referred to by the number of leads that are recorded, for example 3-lead, 5-lead or 12-lead EKGs (sometimes simply "a 12-lead"). A 12-lead EKG is one in which 12 different electrical signals are recorded at approximately the same time and will often be used as a one-off recording of an EKG, traditionally printed out as a paper copy. 3- and 5-lead EKGs tend to be monitored continuously and viewed only on the screen of an appropriate monitoring device, for example during an operation or while being transported in an ambulance. There may or may not be any permanent record of a 3- or 5-lead EKG, depending on the equipment used.

There are generally two types of existing heart monitors: 1) fitness portable monitors having limited capabilities, such as only heart rate, but not ECG waveform, no pre-alert, and poor QRS detector performances; 2) medical grade monitors which are not really portables although they have good performances and provide pre-alerts. Cost of medical grade equipment such as ECG, EMG (electromyogram), EEG (electroencephalogram) is still prohibitive for consumers. Some existing solutions may have good performances but they are not real time. Some others are portable and real time but show poor performances, such as fitness Heart Rate monitors. Medical grade equipment has reasonable performance and generally operates in real time but they are not compact enough for use as portable equipment and are expensive.

BRIEF DESCRIPTION OF THE DRAWINGS

Particular embodiments in accordance with the invention will now be described, by way of example only, and with reference to the accompanying drawings.

Figure 1:
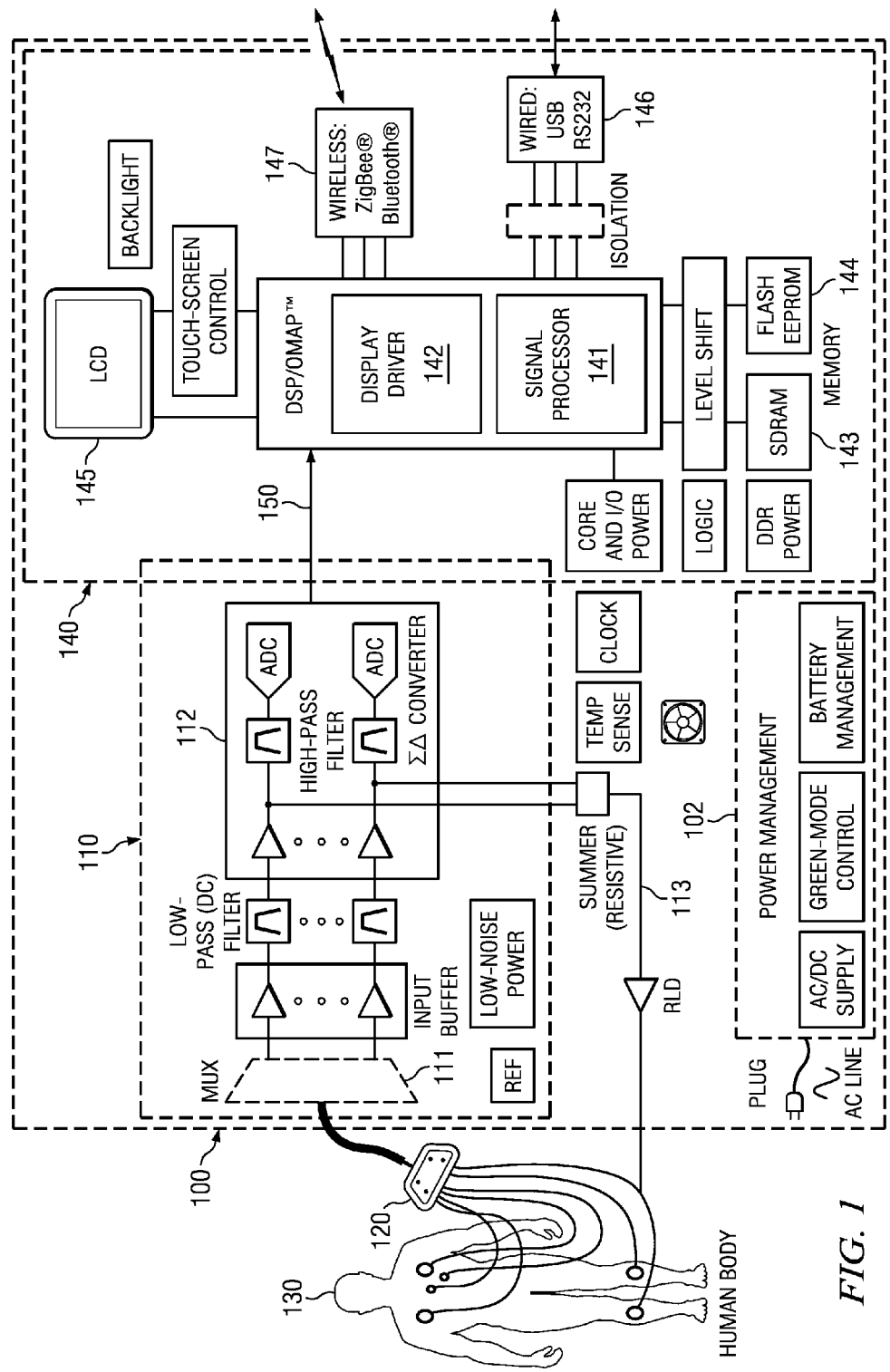
FIG. 1 is a block diagram illustrating an embodiment of the invention within a mobile ECG system.

Other features of the present embodiments will be apparent from the accompanying drawings and from the detailed description that follows.

DETAILED DESCRIPTION OF EMBODIMENTS

Specific embodiments of the invention will now be described in detail with reference to the accompanying figures. Like elements in the various figures are denoted by like reference numerals for consistency. In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Measurement of ECG signal is challenging due to the presence of DC offset and various interference signals. This potential can be up to 300mV for a typical electrode. The interference signals include the 50/60-Hz interference from the power supplies, motion artifacts due to patient movement, radio frequency interference from electro-surgery equipments, defibrillation pulses, pace maker pulses, other monitoring equipment, etc. Embodiments of the present invention allow real time processing and analysis of heart abnormalities with high detection performance, thereby enabling generation of real time pre-alerts in degraded conditions which may be caused by body motions, rubbing or deformation of electrodes, fitness of the person being tested, etc., for example. Embodiments of the invention may be implemented using a suitably equipped mobile consumer device, such as a smart phone, a tablet computer, a personal digital assistant, a personal computer, etc. Other embodiments may be implemented in medical grade fixed or mobile platforms, for example. A QRS detection algorithm that uses several cascaded filters that are coupled to an adaptive filtered threshold through an IIR (infinite impulse response) filter whose cutoff frequency is adapted in real time with logarithmic scaling to the noise level from the original signal will be described in more detail below.

The QRS detection algorithm uses a relative filtered threshold by employing a feedback adaptive IIR filter in which cut-off frequency varies with the signal to noise ratio. The signal to noise ratio is calculated from the peak to average ratio using a sliding window. As a result, the algorithm is able to adapt itself in real time and to provide very accurate QRS detection and PQRST shape preservation even in presence of heavy motion of the user, noise or other artifacts. Therefore user cardiac pre-alerts may be accurately detected.

FIG. 1 is a block diagram illustrating an embodiment of the invention within a mobile ECG system 100. An analog front end section 110 is coupled to a set of leads 120 that are coupled to a subject 130 that is being monitored. Monitored subject 130 is usually a human; however, embodiments of the invention may be used for monitoring other types of subjects such as animal, bird, or reptile, for example. Monitoring leads 120 comprise multiple leads that are attached to various points on subject 130. Typically, three, five, seven, or twelve leads are used for ECG monitoring; however, embodiments of the invention are not limited to any particular number of leads.

Analog front end section 110 may include a multiplexor 111 for selecting various signals from the set of leads 120, EMI (electromagnetic interference) and low pass filtering on each input, and delta-sigma analog-to-digital converters 112 that may include high pass filtering. Right leg drive (RLD) signal 113 may be derived from a selected combination of one or more of the input signals.

Standard monitoring needs frequencies between 0.05-30 Hz. Diagnostic monitoring needs frequencies from 0.05-1000 Hz. Some of the 50 Hz/60 Hz common mode interference can be cancelled with a high input-impedance instrumentation amplifier (INA), which removes the AC line noise common to both inputs. To further reject line power noise, the signal is inverted and driven back into the patient through the right leg by an amplifier. Only a few micro amps or less are required to achieve significant CMR improvement and stay within the UL544 limit. In addition, 50/60 Hz digital notch filters are used to reduce this interference further.

Analog section 110 may be implemented in a single integrated circuit, such as the ADS1294/6/8/4R/6R/8R which is a family of multichannel, simultaneous sampling, 24-bit, delta-sigma analog-to-digital converters (ADCs) with built-in programmable gain amplifiers (PGAs), internal reference, and an onboard oscillator. The ADS1294/6/8/4R/6R/8R incorporates all of the features that are commonly required in medical electrocardiogram (ECG) and electroencephalogram (EEG) applications. ADS129x devices are described in more detail in data sheet SBAS459I, revised January 2012, available from Texas Instruments, which is incorporated by reference herein.

When a low resolution (16 bit) ADC is used, the signal needs to be amplified significantly (typically 100×-200×) to achieve the necessary resolution. When a high resolution (24 bit) sigma delta ADC is used, the signal needs a modest gain, 0-5× for example. Hence a second gain stage and the circuitry needed to eliminate the DC offset may be removed. This leads to an overall reduction in area and cost. The delta sigma approach preserves the entire frequency content of the signal and gives abundant flexibility for digital post processing.

Signal processing section 140 is coupled to receive a stream of digital ECG data 150 from analog section 110. A digital signal processor (DSP) 141 is coupled to non-volatile memory 144 that may store instructions defining various signal processing algorithms. Random access memory (RAM) 143 may be used by DSP 141 for storage of data while performing the various signal processing algorithms. Display driver 142 may be a micro-control unit (MCU) that manages a graphical user interface (GUI) that is displayed on display device 145, which may be a liquid crystal screen (LCD), for example, or any other display device now known or later developed. DSP 141 and MCU 142 may be implemented in a single IC, such as an OMAP (Open Multimedia Application Platform) device available from Texas Instruments, for example. Other embodiments may use other implementations of processors or signal processors that are now known or later developed. For example, various types of system on a chip (SoC) ICs may contain two to sixteen, or more DSP cores, for example.

One or more wired interfaces 146 may be provided that support USB (Universal Serial Bus), RS232, or other types of wire interfaces for transferring processed ECG signals to another system for further evaluation. One or more wireless interfaces 147 may be provided that support ZigBee, Bluetooth, or other types of wireless interfaces for transferring processed ECG signals to another system for further evaluation. Furthermore, a wireless interface 147 may also be provided for sending processed ECG signals to a remote system via a cellular phone or data network, for example.

Power management logic 102, clock, temperature sensing logic and fan control logic may also be included in ECG system 100 to provide power and temperature control for analog system 110 and DSP system 140.

Note that most or all of the components included within signal processing section 140 may now be available within a mobile handset, such as a smart phone, that may be programmed to provide the needed signal processing. Previously, the cost of ECG, EMG, and EEG equipment was prohibitive for consumer type devices. Coupling an analog front end section 110 to a smart phone may provide a cost effective medical monitoring device when the smart phone is programmed to perform ECG processing, as will be described in more detail below.

Figure 2:
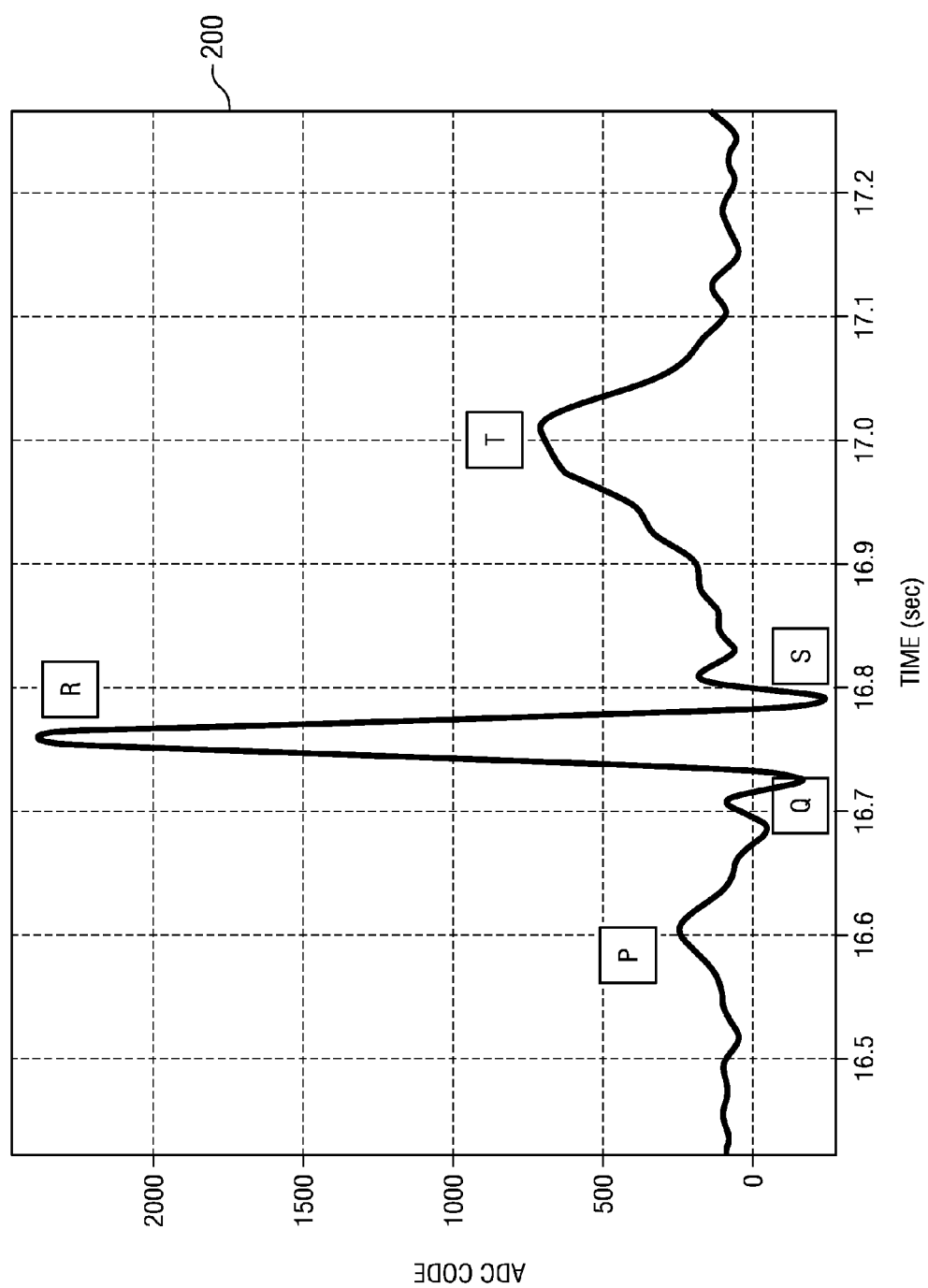
FIGS. 2-3 illustrate ECG plots that are analyzed by the mobile ECG system of FIG. 1.

FIG. 2 is a plot 200 illustrating a typical heart beat cycle. Like other biomedical signals, ECG is considered as a non stationary process. Its mean value and its standard deviation vary over the time. However, it contains useful information that can be interpreted as a pseudo deterministic pattern, referred to as a PQRST pattern. During each heartbeat a healthy heart will have an orderly progression of a wave of depolarisation that is triggered by the cells in the sinoatrial node, spreads out through the atrium, passes through "intrinsic conduction pathways" and then spreads all over the ventricles. The normal ECG (EKG) is composed of a P wave, a QRS complex and a T wave. The P wave represents atrial depolarization and the QRS represents ventricular depolarization. The T wave reflects the phase of rapid repolarization of the ventricles.

There are several abnormalities that may be noted when a PQRST wave is analyzed. They may include one or more of the following:

Inversion in leads where the P is normally upright or the presence of an upright P wave in aVr. This change is often found in conditions where the impulse travels through the atria via an abnormal pathway, such as ectopic atrial or A-V nodal rhythms;

Increased Amplitude usually indicates atrial hypertrophy and is found especially in A-V valvular disease, hypertension, cor-pulmonale, and congenital heart disease;

Increased Width often indicates left atrial enlargement or diseased atrial muscle;

Biphasity is a notable sign of left atrial enlargement when the second half of the P wave is significantly negative in leads III and V1;

Notching In P-Mitrale: the P often is wide and notched and is taller in lead I than in lead III. Notching is considered significant when the distance between peaks is greater than 0.04 seconds;

Peaking indicates right atrial strain. These tall pointed P waves are often taller in lead III than in lead I. This is known as P-Pulmonale;

Absence of P waves occurs in A-V nodal rhythms and S-A Block.

Figure 3:
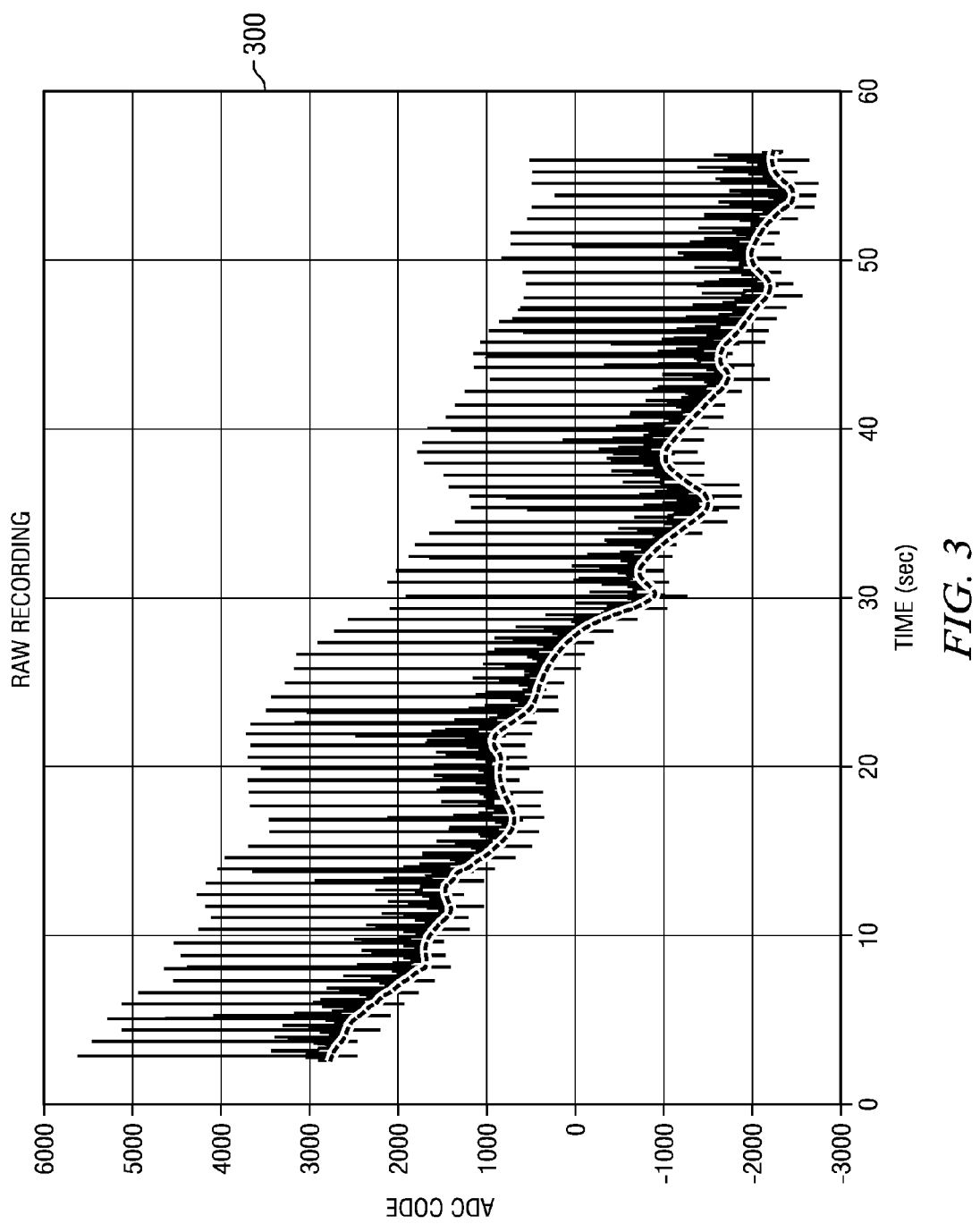

FIG. 3 is a plot 300 illustrating a sequence of raw ECG data 150 received from analog section 110, referring back to FIG. 1, over a period of about fifty seconds. In this embodiment, the analog-to-digital (ADC) code value is based on a 24 bit converter. Other embodiments may use different values based on different ADC converter precision. Noise, artifacts, EMG (electromyogram) interference from other muscles in the body, breathing, 60 Hz interference from power lines, etc may make simple analysis of ECG difficult. In order to preserve PQRST information, a bandwidth of approximately 3 Hz to 30 Hz may need to be provided. In some embodiments, a bandwidth up to approximately 1000 Hz may add accuracy.

Figure 4:
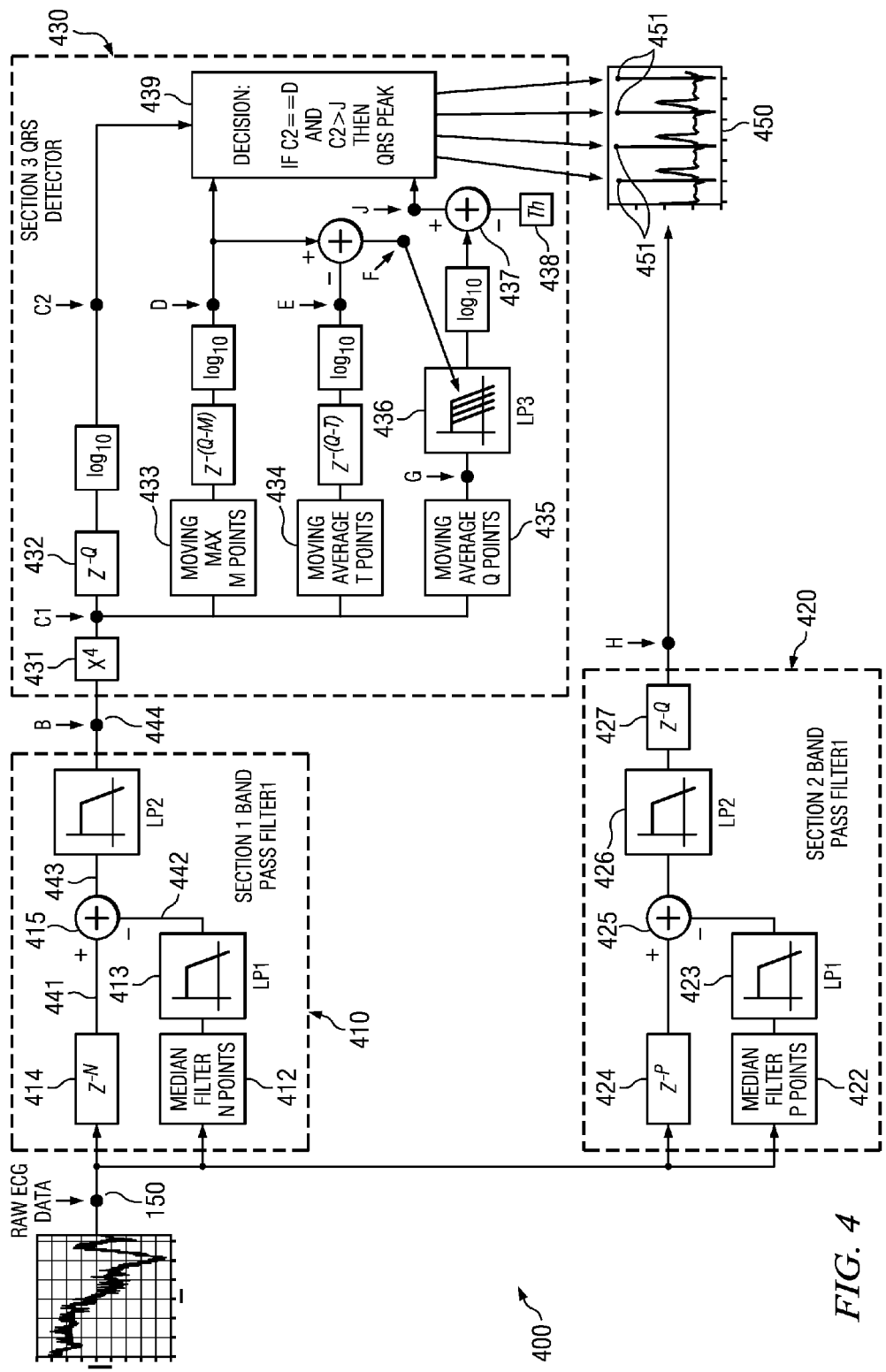
FIG. 4 is a schematic illustration of a real-time ECG filter implemented by the ECG system of FIG. 1.

FIG. 4 is a schematic illustration of a real-time ECG filter 400 implemented by the ECG system of FIG. 1. Robust detection of each QRS wave is important for further digital processing of an ECG sequence. A detector should work even when signal to noise ratio (SNR) is degraded. In this embodiment, the ECG filter is partitioned into three sections; section one 410 band pass filter, section two 420 band pass filter, and section three 430 QRS detector. A stream of raw ECG 150 is received from analog front end section 110, referring back to FIG. 1. Typically, it will include interference and distortion, as discussed with regard to FIG. 3. Embodiments of real-time ECG filters described herein were tested against the MIT-BIH database that includes 48 records, 30 minutes each, file based. This is a reference benchmark that is widely used for testing QRS detection algorithms. Embodiments described herein obtained 99.7% sensitivity and 99.9% positive predictability, similar to medical grade equipment using more complex non-real time algorithms.

Section two 420 is intended to provide a band-pass filtered ECG ready for cardiologist interpretation. In this embodiment, the raw data ECG is recorded by analog front-end 110 using a sampling frequency of 250 Hz. In another embodiment, a higher or a lower sampling frequency may be used. The ECG raw data is filtered in non linear manner using median filter (P points) 422 so that all high frequency components are removed and then conveyed through low pass filter LP1 423 in order to remove the remaining median filter noise. The same ECG raw data is delayed 424 by P samples and the output of LP1 filter 423 is subtracted 425 from it so that baseline wander of the ECG is suppressed. This combination of median filter 422, LP1 filter 423, and subtraction 425 from the original delayed signal is equivalent to high pass filtering. Low pass filter LP2 426 is a 5th order filter that has a cut-off frequency of 33 Hz and produces a filtered ECG signal H that is delayed 427 in order to align with the results from section three 430. Output signal H is ready for cardiologist interpretation. An example of filtered ECG signal H is illustrated at 450. By using an appropriate value for P, the overall PQRST wave is preserved and not distorted. Typically, a value for P may be selected to be P=Fs/2, for example.

Section one 410 is intended to prepare the ECG signal for beat detector 430. It is identical to section two except median filter 412 is changed to have a point value of (N). By selecting an appropriate value for N, baseline wander, P wave and T wave are also suppressed on this section; such that only a QRS portion of the signal is preserved for further processing as signal B 444. Typically, a value for N may be selected to be N=Fs/10, for example.

Section three 430 represents the QRS detector itself. In order to amplify the high frequency content of a QRS wave, signal B is squared twice 431 to produce signal C1. From signal C1 three threshold signals are derived as follows. Signal C1 is scaled non-linearly to form signal C2. Each sample k of the signal C2 is produced as a logarithm on base 10, delayed 432 by Q samples, as indicated by equation (1).

$$C2_k = \log 10(C1_k) \tag{1}$$

A first threshold signal is signal D. Each sample k of the signal D is produced using a moving maximum 433 using M points sliding window on the signal C1, taken as a logarithm on base 10 and delayed by Q-M samples, as indicated by equation (2). Thus, signal D represents peak values of signal C1.

$$D_k = \log 10(\max(C_1(k) \ldots C_1(k+M))) \tag{2}$$

A second threshold signal is signal E. Each sample k of the signal E is produced using a moving average 434 using T points sliding window on the signal C1, taken as logarithm on base 10 and delayed by Q-T samples as indicated by equation (3). Thus, signal E represents average values of signal C1 over the window range.

$$E_k = \log 10\left(\frac{\left(\sum_{m=0}^{m=M-1} C_1(k+m)\right)}{M}\right) \tag{3}$$

A third threshold signal is signal G. Each k sample of the signal G is obtained using a moving max using Q points sliding window on the signal C1 as indicated by equation (4)

$$G_k = (\max(C_1(k) \ldots C_1(k+Q))) \tag{4}$$

Figure 5:
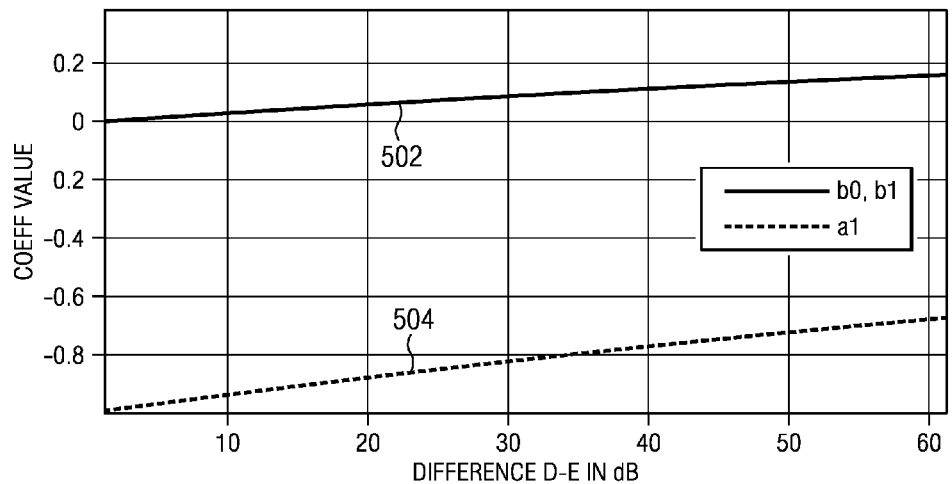
FIG. 5 is a plot of a quasi-linear regression used by the filter of FIG. 4.
Figure 6:
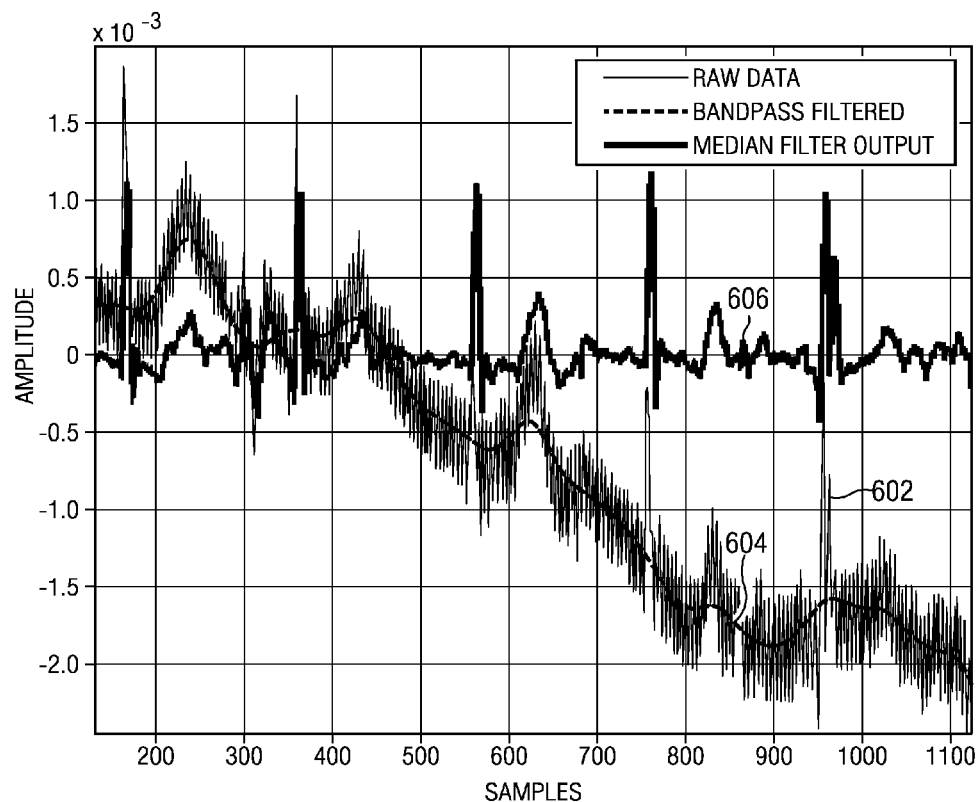
FIGS. 6, 7A-7D illustrate wave forms produced during analysis of ECG signals by the real-time ECG filter of FIG. 4.

Signal G is passed through a filter LP3 436 having a transfer function according to equation (5).

$$H(z) = \frac{b_0 + b_1 \cdot z^{-1}}{1 + a_1 \cdot z^{-1}} \tag{5}$$

where, the coefficients a1, b0, b1 are dynamically calculated as a function of difference between the signal D and the signal E according to equation (6).

$$F_k = s \cdot (D_k - E_k) \tag{6}$$

where s is a scaling constant. Coefficients a0,a1,b0,b1 are then obtained from a quasi-linear regression as shown FIG. 5, where plot line 502 represents coefficients b0 and b1 and plot line 504 represents coefficient a1 as a function $F_k$.

The a1, b0, b1 were calculated (iteratively for Fc=[1-10 Hz]) using known methods available in environments such as Matlab, Octave, etc. For instance, the function [B,A] =BUT- TER(N,Wn), returns b0 and b1 and a0 in [B,A] vectors by using in input N=order and Wn=2*pi*Fc/Sampling freq. The algorithm behind this is:

Choose the cut-off frequency Fc and filter order (Fc=[1-10 Hz] and order is 1);

For each pair of Fc and order derive the corresponding analog transfer function;

Use bilinear transform applied to get the corresponding digital coefficients.

In this embodiment, the variations of b0, b1 and a1 versus cutoff frequency Fc are qasilinear and can be written: b0=b1=0.034*Fc+0.064; a1=0.022*Fc+0.99. The cutoff frequency value Fc=[1-10 Hz] may be substituted in the equations for every sample with Fk from equation (6) by appropriate scaling. For example, a value of Fk=0 translates into Fc=1 Hz and 100 dB valuef of Fk corresponds to 10 Hz Fc.

A third threshold signal J is formed from the output of the filter H(z) 436 expressed in dB shifted down 437 by threshold 438, which in this example is selected to be: threshold=6 dB. As explained above, signal Fk is proportional to the difference between Dk and Ek, therefore proportional to the ratio (difference in dB) between the peak and the average of the signal C1. When the ECG signal is noisy, the Peak to Average Ratio is low, therefore the cutoff frequency of H (z) is low and the J signal (which is the main threshold) is strongly low-pass filtered in order to avoid false detections. When signal C1 is clean, the cut-off frequency of LP3 increases and the J signal is less low pass filtered and therefore can follow the low values of C1 signal. This avoids missing beats (false negative). Each decision of beat detector 439 is performed using the signal C2, D and J. If C2==J and C2>D then the QRS peak is considered as a true beat (where "==" means C2 is equal to J). It is worth noting that C2 is equal to J only on a single point for each beat. Therefore, the beats may now be annotated on signal H that is provided as the output of section two 420.

An example signal H is illustrated at 450 with annotated heartbeats indicated at 451. The annotation may be provided along with signal 450 for use by a cardiologist while interpreting filtered ECG signal 450.

Heart rate may be computed as follows as indicated by equation (7).

$$HR = \frac{60 \cdot B_{nb}}{T} = \frac{60 \cdot B_{nb} \cdot Fs}{N} \text{ [beats/minute]} \quad (7)$$

where:
$B_{nb}$ is the number of detected beats
$F_s$ is sampling frequency
N is number of acquired samples
T is the observation window, seconds FIGS. 6, 7A-7D illustrate wave forms produced during analysis of ECG signals by the real-time ECG filter 400. Plot line 602 represents the raw, delayed ECG data output by delay 414 at point 441 of section one 410 of real time filter 400, referring to FIG. 4. Plot line 604 represents the band pass filtered ECG signal output by band pass filter 413 at point 442. Plot 606 represents the median filtered signal 443 produced by subtraction 415 and illustrates that baseline wander is suppressed and that T wave is also suppressed.

Figure 7A:
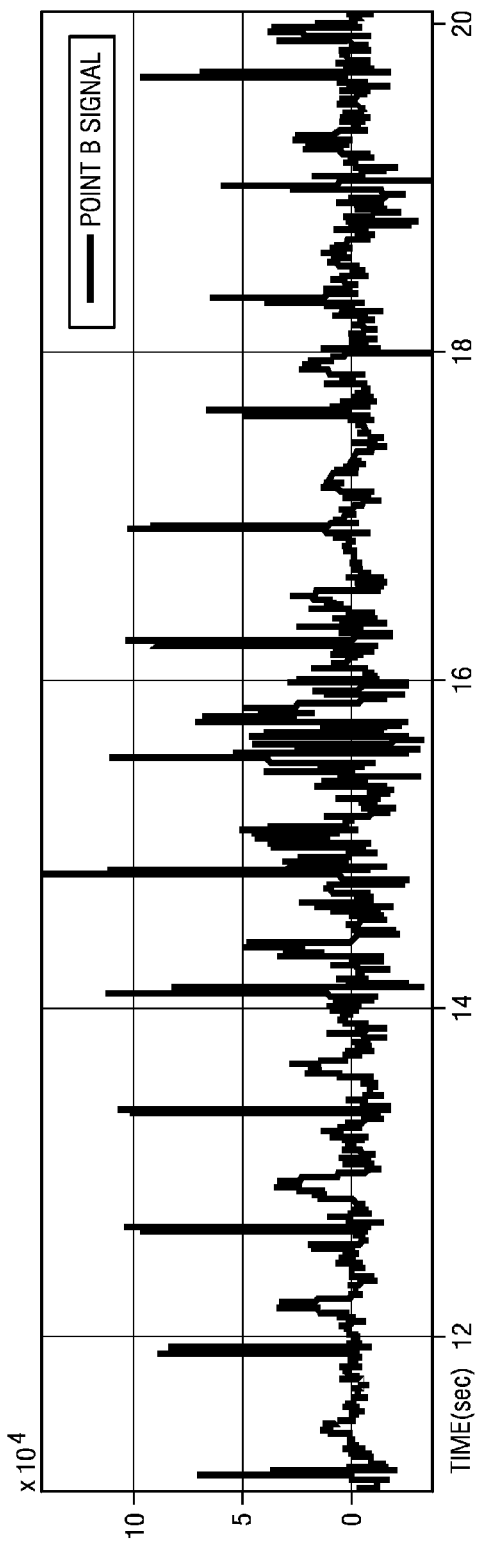
Figure 7B:
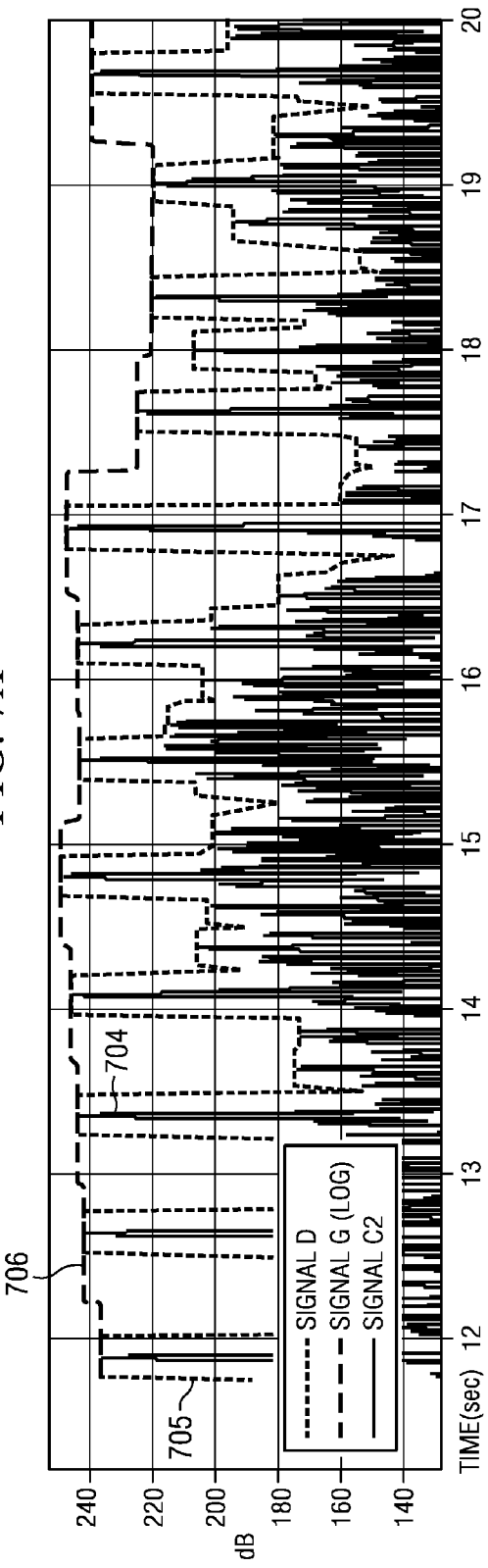
Figure 7C:
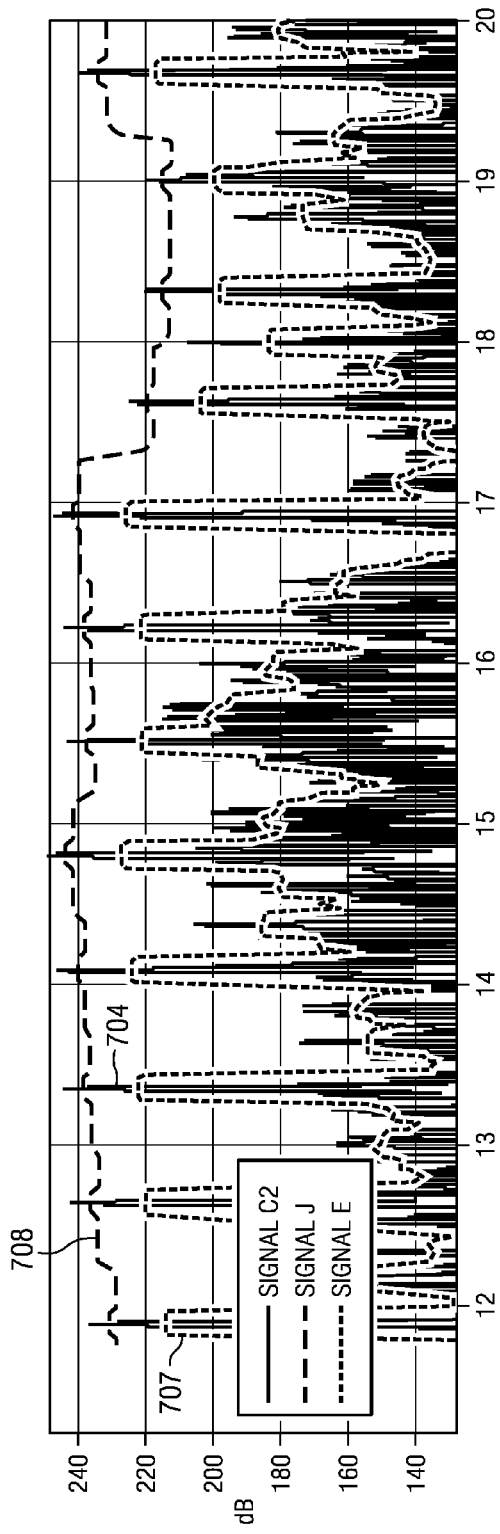
Figure 7D:
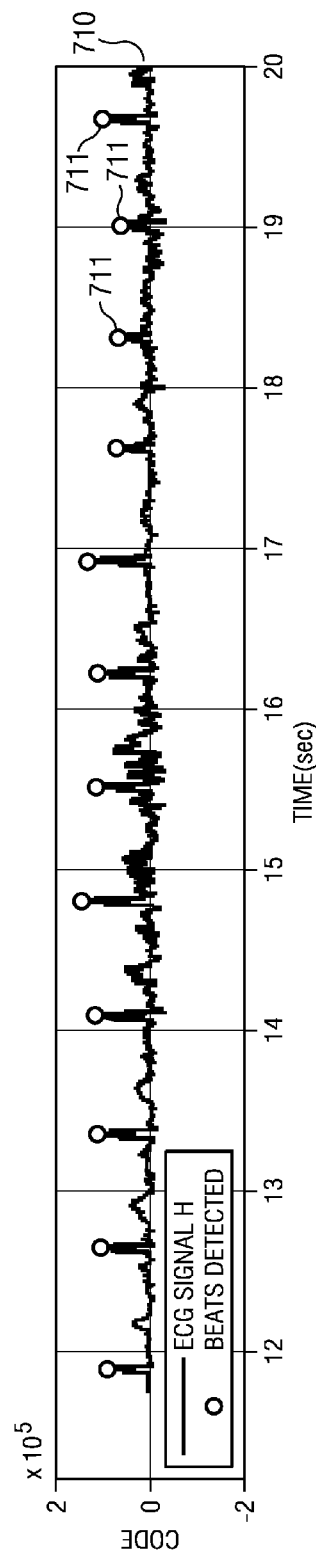

FIG. 7A illustrates a representative signal B that is input to section three 430 of real time filter 400. In FIG. 7B, plot line 704 represents signal C2, plot line 705 represents signal D, and plot line 706 represents signal D. In FIG. 7C, plot line 704 represents signal C2, plot line 707 represents signal E, and plot line 708 represents signal J. In FIG. 7D, plot line 710 represents signal H, and dots indicated at 711 represent detected heart beats. As described above, signal H may be transferred in real time to a cardiologist for analysis.

Figure 8:
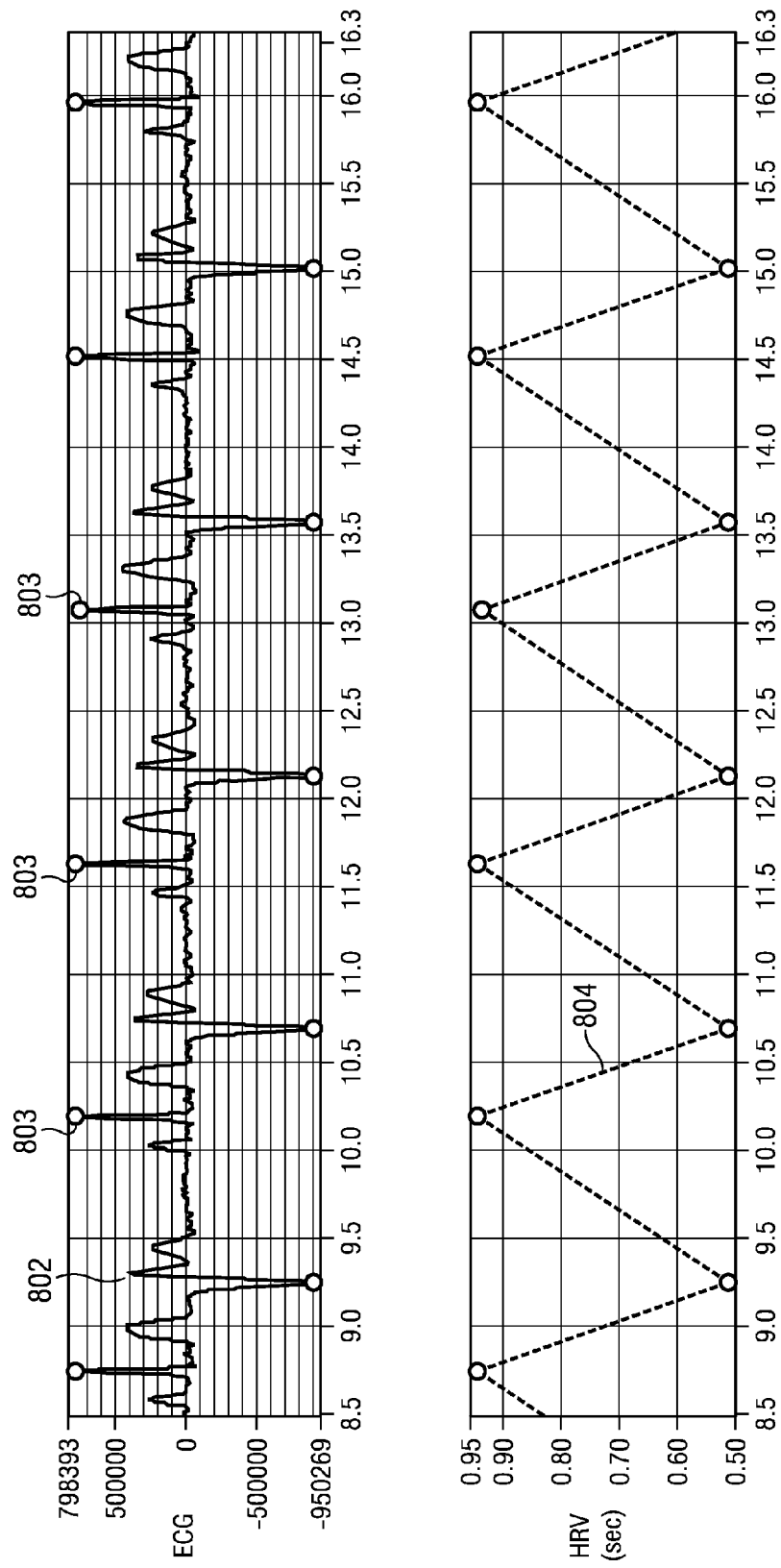
FIGS. 8-9 are timing diagrams illustrating detection of alert conditions by the ECG system of FIG. 1.
Figure 9:
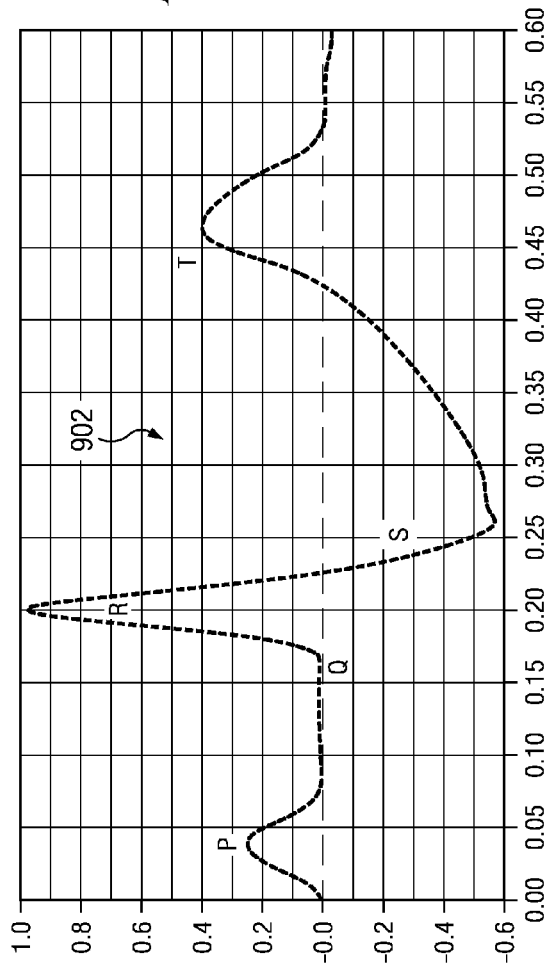

FIGS. 8-9 are timing diagrams illustrating detection of pre-alert conditions indicated by anomalies in the ECG data by the ECG system of FIG. 1. FIG. 8 illustrates detection of heart rate variability (HRV), which is the time difference between two consecutive beats (R-R interval) over time. Plot 802 is an example ECG signal H, referring to FIG. 4, that may be further analyzed to detect alert conditions. Detected heart beats are annotated as described above as indicated at 803. A simple HRV detection function may detect HRV by comparing the timing of each annotated heart beat 803. If the HRV shows significant and sharp variations, it may indicate a condition referred to as bigeminy.

Bigeminy refers to a slightly abnormal heart rhythm that is usually of no serious concern in the absence of other cardiovascular disease. This condition describes a state where a heart alternates one "normal" beat with one "premature" beat. The term "normal sinus rhythm" describes the normal beating of the heart, where electrical impulses originate in the sinus node (SA node), travel through the atria and atrioventricular node (AV node), and terminate in the ventricles. Premature beats occur when either the atria or the ventricle initiate their own electrical impulse before receiving the impulse from the sinus node. The term "bigeminy" is typically used to describe when normal sinus beats alternate with premature ventricular beats.

FIG. 9 illustrates another condition referred to as large ST segment depletion, as indicated at 902, that may be easily detected and used to trigger a pre-alert in real time. ECG signal H, referring to FIG. 4, may be further analyzed to detect large ST depletion by determining if the S point after a detected heart beat regularly falls below a specified negative threshold.

While FIGS. 8-9 illustrate two different types of anomalies, it should be understood that there are many types of anomalies that may be detected in real time by analysis of ECG signals after they have been filtered and heart beats detected as described above.

Figure 10:
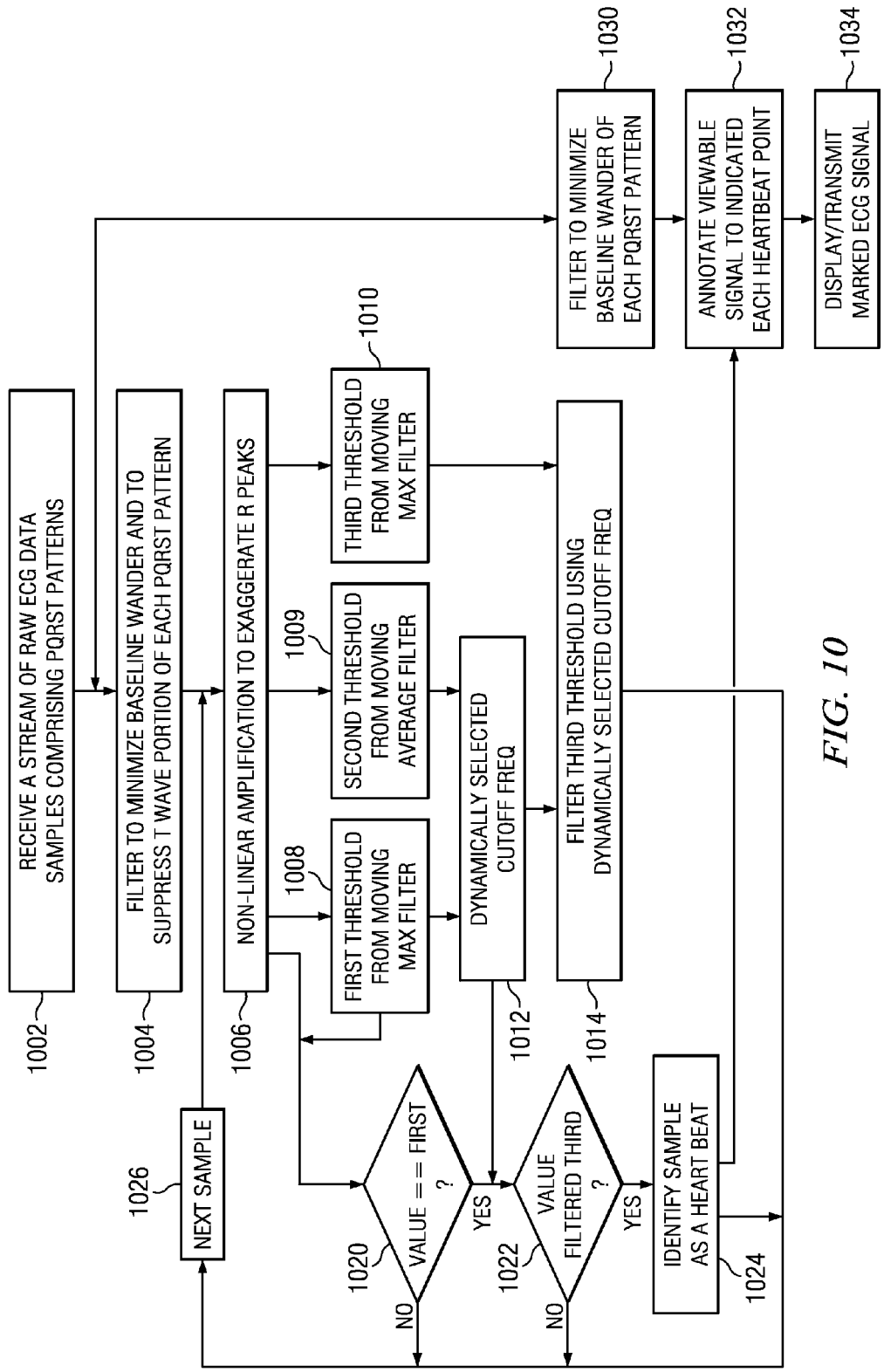
FIG. 10 is a flow chart illustrating operation of ECG analysis by the ECG system.

FIG. 10 is a flow chart illustrating operation of ECG analysis by the ECG system described above. A stream of raw ECG data samples is received 1002 from an analog front end subsystem that samples and converts ECG signals into a stream of ECG data samples, as described in more detail above. The stream of ECG data samples represents a periodic sequence of PQRST patterns.

The raw ECG data is filtered 1004 to form filtered ECG data by using a non-linear filter to minimize baseline wander and to suppress a T wave portion of each PQRST pattern. Filtering 1004 of the raw ECG data may be done by filtering the raw ECG data using a cascade of median filter and low pass filter, delaying the raw ECG data, and subtracting an output signal of the low pass filter from the delayed raw ECG data in order to deliver a high pass filtered data.

A non-linear operation is performed 1006 on the filtered ECG data to form an amplified signal that exaggerates an R peak of each PQRST pattern. The amplified signal may be formed by squaring the filtered ECG data at least one time. In this embodiment the ECG data is squared twice.

A first threshold signal is formed 1008 using a moving max filter on the amplified signal. Similarly, a third threshold signal is formed 1010 using a moving max filter on the amplified signal. The first threshold signal and the third threshold signal may be derived using a first window width for the first threshold signal and a different window width for the third threshold signal.

A second threshold signal is derived 1009 using a moving average filter on the amplified signal.

The third threshold signal is filtered 1014 to form a filtered threshold signal using a filter in which a cutoff frequency is dynamically selected 1012 as a function of the first threshold signal and the second threshold signal. Filtering the third threshold signal may be performed by filtering the third threshold signal with a first order infinite impulse response (IIR) filter and dynamically selecting a cutoff frequency 1012 for the IIR as a linear function of a difference between a logarithm of the first threshold signal 1008 and a logarithm of the second threshold signal 1008.

In another embodiment, filtering 1014 the third threshold signal may be performed by filtering the third threshold signal with a first order infinite impulse response (IIR) filter and dynamically selecting 1012 a cutoff frequency for the IIR as a linear function of a ratio of the first threshold signal 1008 and the second threshold signal 1009.

A sample in the amplified signal is indentified 1024 to be a heart beat point only when the sample value is equal 1020 to the first threshold signal 1008 and greater than 1022 the filtered threshold signal 1014.

The raw ECG data may also be filtered 1030 using a non-linear filter to minimize baseline wander of each PQRST pattern to form a viewable ECG signal. The viewable ECG signal may be annotated 1032 to indicate each heart beat point. The annotated viewable ECG signal may then be displayed 1034 on a local display device or transmitted to a remote location for viewing by a cardiologist, for example. Filtering 1030 the raw ECG data may be performed by filtering the raw ECG data using a cascade of median filter and low pass filter, delaying the raw ECG data, and subtracting an output signal of the low pass filter from the delayed raw ECG data in order to deliver a high pass filtered data.

Figure 11:
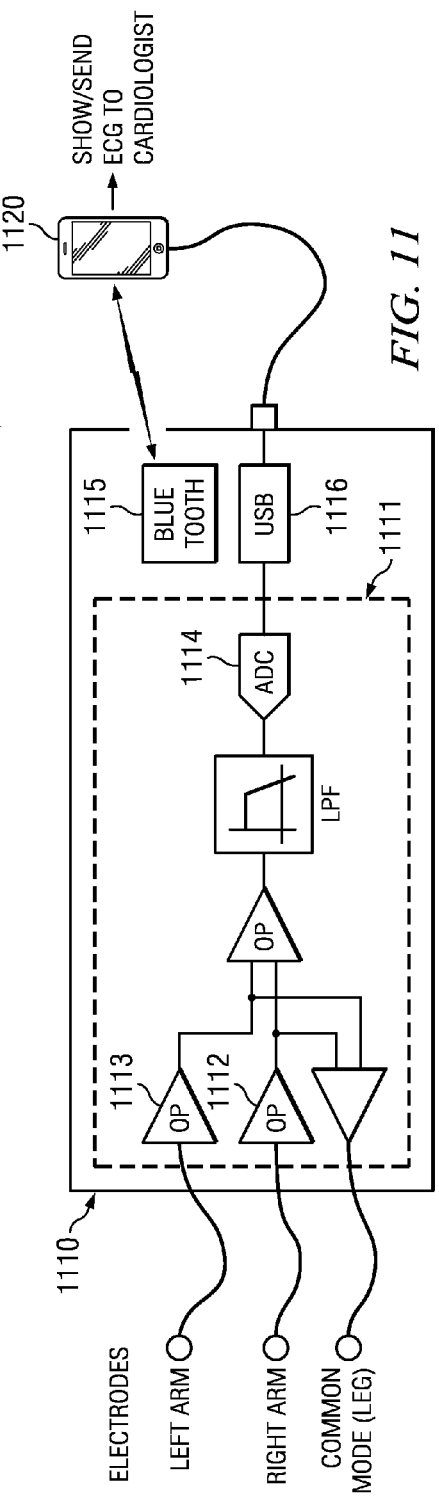
FIG. 11 illustrates another embodiment of a mobile ECG system that utilizes a mobile handset.

FIG. 11 illustrates another embodiment of a mobile ECG system 1100 that utilizes a mobile handset 1120. Analog front end module 1110 may include high-impedance inputs for the various electrode leads, such as op-amps 1112, 1113. Analog to digital converter 1114 converts low pass filtered analog signals to digital representations. In this embodiment, ADC 1114 has a precision of 24 bits. In other embodiments, ADC with greater or lesser precision may be used. Three electrode leads are illustrated in this example, which is useful for sports and simple monitoring uses. Other embodiments may include more electrode leads, as discussed in more detail above.

Analog section 1111 may be implemented in a single integrated circuit, such as the ADS1294/6/8/4R/6R/8R which is a family of multichannel, simultaneous sampling, 24-bit, delta-sigma analog-to-digital converters (ADCs) with built-in programmable gain amplifiers (PGAs), internal reference, and an onboard oscillator. The ADS1294/6/8/4R/6R/8R incorporates all of the features that are commonly required in medical electrocardiogram (ECG) and electroencephalogram (EEG) applications.

USB function 1116 may transmit the digital sequence of ECG samples produced by ADC to a USB input on mobile phone 1120. Alternatively, a Blue Tooth transmitter circuit 1115 may be included to wirelessly transmit the digital sequence of ECG samples produced by ADC to a Blue Tooth receiver on mobile phone 1120.

Mobile phone 1120 is representative of any of several smart phones that are available from a variety of vendors. A smart phone typically includes signal processing hardware and capabilities that are similar to signal processing section 140 of FIG. 1. Application software, also referred to as an "app," may be downloaded into the phone using the normal app download process for that smart phone. The app is configured to perform the filtering, thresholding, and QRT detection functions that are described in more detail above by executing software instructions stored in memory that is accessible by a DSP processor, or other type of processor, that is included within smart phone 1120. As described in more detail above, the application may monitor the processed ECG signal and provide heart beat information, along with detecting various alert conditions, such as HRV, bigeminy, and large ST segment depletion, for example.

The electrodes may be connected to a subject, such as a person or animal, to monitor the performance of the subject's heart in real-time. The ECG app may display an ECG signal on a display screen of the smart phone, for example. The ECG app may display ECG pre-alerts on the display screen, or sound an audible alert using a speaker that is included within the smart phone, for example. The ECG app may also forward the filtered ECG signal, equivalent to signal H on FIG. 4, in real-time to a remote monitoring system using the data transmission capabilities that are included within the smart phone, for example. The ECG app may also forward pre-alert conditions that it has detected to the remote monitoring system.

The remote monitoring system may be located in a hospital or in a doctor's office, for example. A cardiologist may immediately review the ECG signal and associated pre-alert information on the remote monitoring system. The cardiologist may interact with the subject using the voice channel of the smart phone while ECG data continues to be transmitted to the remote site using a data channel of the smart phone.

Figure 12A:
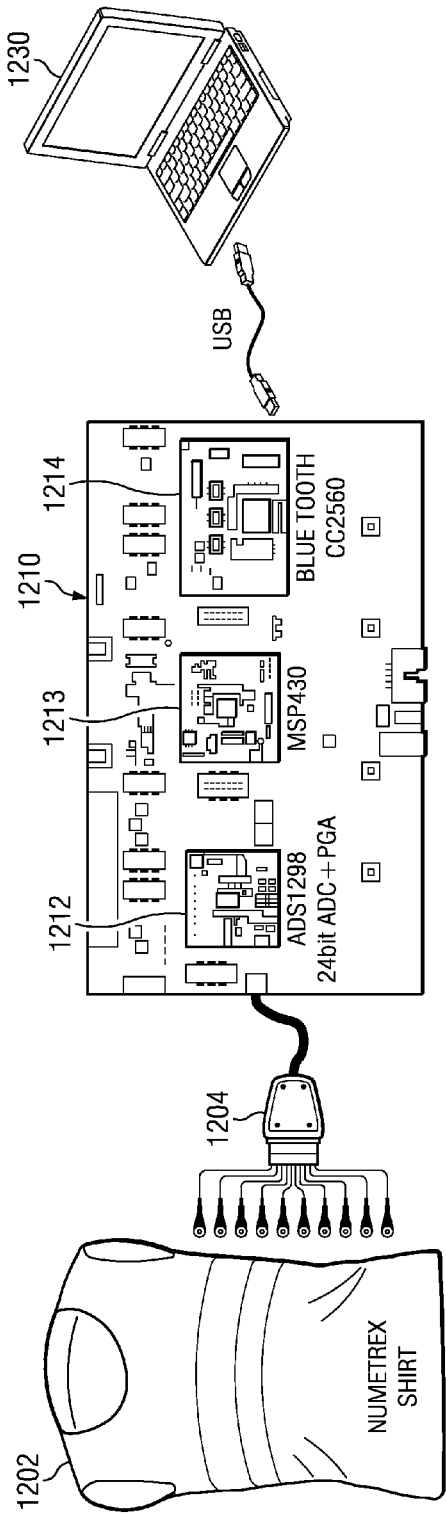
FIGS. 12A-12B illustrate other embodiments of a mobile ECG system.

FIG. 12A illustrates other embodiments of a mobile ECG system. In this example, analog front end module 1210 may be coupled to a set of leads 1204 that are in turn coupled to termination points on a shirt 1202 that includes electrodes that are affixed to the shirt and arranged to make skin contact with a subject when shirt 1202 is worn by the subject. An example of shirt 1202 is a NuMetrex shirt or sports bra, available from Textronics.

Front end module 1210 is similar to front end module 1110, and may be implemented to support twelve ECG leads, for example, or a fewer number of ECG leads. Front end module may be implemented using an ADS1294 analog to digital converter 1212, as described in more detail above. A microcontroller may be coupled to ADC 1212 and control data transmission from ADC 1212 to a USB output. The microcontroller may also be coupled to a blue tooth circuit 1214 and thereby control wireless transmission of data from ADC 1212. Microcontroller 1213 may be a MSP430 device, available from Texas Instruments, for example. Blue tooth circuit 1214 may be a CC2560 device, available from Texas Instruments, for example.

A USB cable may be used to couple front end module 1210 to a laptop 1230, for example. Laptop 1230 is representative of any number of known portable computers that include sufficient processing power to perform the real-time filtering and QRS identification described in more detail above. Laptop 1230 is configured to receive a stream of ECG data from front end module 1210. Laptop 1230 is also configured with a software application that makes use of the processor included within laptop 1230 to process a stream of ECG data transmitted from a subject that is wearing shirt 1202.

The app is configured to perform the filtering, thresholding, and QRT detection functions that are described in more detail above by executing software instructions stored in memory that is accessible by a DSP processor that is included within computer 1230. As described in more detail above, the application may monitor the processed ECG signal and provide heart beat information, along with detecting various pre-alert conditions, such as HRV, bigeminy, and large ST segment depletion, for example.

The electrodes may be connected to a subject, such as a person or animal, to monitor the performance of the subject's heart in real-time. The ECG app may display an ECG signal on a display screen of laptop computer 1230, for example. The ECG app may display ECG pre-alerts on the display screen, or sound an audible alert using a speaker that is included within the laptop computer, for example. The ECG app may also forward the filtered ECG signal, equivalent to signal H on FIG. 4, in real-time to a remote monitoring system using the data transmission capabilities that are included within the laptop computer, for example. The ECG app may also forward alert conditions that it has detected to the remote monitoring system. Transmission to the remote monitoring site may be done via the internet, for example, used a wired or wireless connection included within laptop computer 1230.

The remote monitoring system may be located in a hospital or in a doctor's office, for example. A cardiologist may immediately review the ECG signal and associated alert information on the remote monitoring system. The cardiologist may interact with the subject using the voice channel on the laptop computer, such as voice over internet, while ECG data continues to be transmitted to the remote site using a data channel of the laptop computer.

Figure 12B:
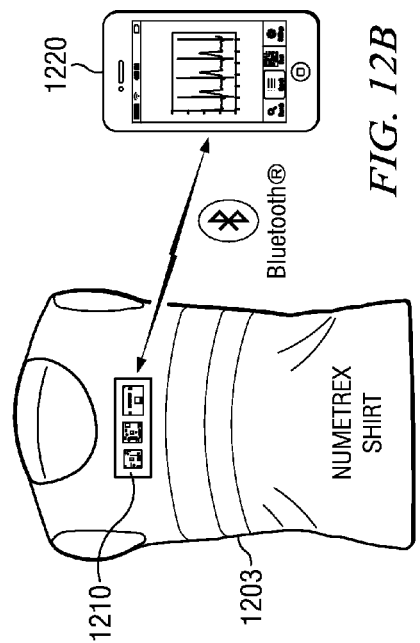

FIG. 12B illustrates another embodiment of a mobile ECG system. In this example, analog front end module 1210 is attached to shirt 1203 and be coupled to a set of termination points on shirt 1203 that includes electrodes that are affixed to the shirt and arranged to make skin contact with a subject when shirt 1203 is worn by the subject. An example of shirt 1203 is a NuMetrex shirt or sports bra that is suitably modified to carry analog front end module 1210.

Analog front end module 1210 is configured to wirelessly transmit ECG data collected from a subject that is wearing shirt 1203 to a nearby blue tooth receiver located in smart phone 1220, for example. Smart phone 1220 is configured with an ECG app, as described in more detail above, and may thereby process and display the ECG data in real time and also transmit the ECG data to a remote site for analysis by a cardiologist or other health care giver.

Thus, a low cost, mobile system has been described that provides real time QRS detection performance that is better than published existing research. There is no need for any learning phase as is required by many prior algorithms. Various embodiments may provide additional heart information beyond the just heart rate by analyzing PQRST waveforms; this may allow various embodiments to provide real-time pre-alerts for various conditions. These low cost, mobile systems may be useful for home use, fitness use, etc.

Other Embodiments

While the invention has been described with reference to illustrative embodiments, this description is not intended to be construed in a limiting sense. Various other embodiments of the invention will be apparent to persons skilled in the art upon reference to this description. For example, the analog front end section may be packaged in various manners now known or later developed that will provide protection and ease of use. For example, the package may be waterproof and rugged so that the analog front end may be permanently attached to a shirt or sports bra and survive normal use and cleaning processes.

The analog front end may be battery powered, or it may be packaged with an energy scavenging unit that derives power from motion of the test subject, solar energy, etc.

While a wired USB link or a wireless blue tooth link have been described, other embodiments may use any sort of known or later developed wired (metallic or optical) or wireless interconnect protocol that supports the necessary transfer rate to support real-time transmission of filtered ECG data. Of course, the necessary transfer rate will depend on the ADC precision and sample rate selected for the embodiment.

While a personal computer and a smart phone were described herein for providing the requisite signal processing to perform the filtering and detection functions, other types of mobile consumer devices may be used to implement the filtering and detection functions described herein, such as a tablet computer, a personal digital assistant, etc. In general, as used herein, a consumer device is a general purpose device that may be used by a consumer for other tasks in additional to providing ECG monitoring.

While logarithmic scaling of the thresholds was described herein, another embodiment may use another form of non-linear scaling. Another embodiment may use linear representations and use ratios instead of differences for comparing threshold values.

In other embodiments, the requisite signal processing to perform the filtering and detection functions may be provided by a digital processing system designed explicitly for ECG use, by a non-mobile system, a medical grade system, etc.

While the systems described herein may be capable of transmitting filtered ECG data to a remote site in real time, other embodiments may provide a storage function to store a portion of filtered ECG data for later transfer to a remote system.

Embodiments of the filters and methods described herein may be provided on any of several types of digital systems: digital signal processors (DSPs), general purpose programmable processors, application specific circuits, or systems on a chip (SoC) such as combinations of a DSP and a reduced instruction set (RISC) processor together with various specialized accelerators. An SoC may contain one or more mega-cells which each include custom designed functional circuits combined with pre-designed functional circuits provided by a design library.

The techniques described in this disclosure may be implemented in hardware, software, firmware, or any combination thereof. If implemented in software, the software may be executed in one or more processors, such as a microprocessor, application specific integrated circuit (ASIC), field programmable gate array (FPGA), or digital signal processor (DSP). The software that executes the techniques may be initially stored in a computer-readable medium such as compact disc (CD), a diskette, a tape, a file, memory, or any other computer readable storage device and loaded and executed in the processor. In some cases, the software may also be sold in a computer program product, which includes the computer-readable medium and packaging materials for the computer-readable medium. In some cases, the software instructions may be distributed via removable computer readable media (e.g., floppy disk, optical disk, flash memory, USB key), via a transmission path from computer readable media on another digital system, etc.

Certain terms are used throughout the description and the claims to refer to particular system components. As one skilled in the art will appreciate, components in digital systems may be referred to by different names and/or may be combined in ways not shown herein without departing from the described functionality. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple"

and derivatives thereof are intended to mean an indirect, direct, optical, and/or wireless electrical connection. Thus, if a first device couples to a second device, that connection may be through a direct electrical connection, through an indirect electrical connection via other devices and connections, through an optical electrical connection, and/or through a wireless electrical connection.

Although method steps may be presented and described herein in a sequential fashion, one or more of the steps shown and described may be omitted, repeated, performed concurrently, and/or performed in a different order than the order shown in the figures and/or described herein. Accordingly, embodiments of the invention should not be considered limited to the specific ordering of steps shown in the figures and/or described herein.

It is therefore contemplated that the appended claims will cover any such modifications of the embodiments as fall within the true scope and spirit of the invention.

What is claimed is:

1. A method for processing ECG data, the method comprising:
   receiving a stream of raw ECG data samples comprising PQRST patterns;
   filtering the raw ECG data to form filtered ECG data by using a non-linear filter to minimize baseline wander and to suppress a T wave portion of each PQRST pattern;
   performing a non-linear operation on the filtered ECG data to form an amplified signal that exaggerates an R peak of each PQRST pattern;
   deriving a first threshold signal and a third threshold signal using a moving max filter on the amplified signal;
   deriving a second threshold signal using a moving average filter on the amplified signal;
   filtering the third threshold signal to form a filtered threshold signal using a filter in which a cutoff frequency is dynamically selected as a function of the first threshold signal and the second threshold signal; and
   identifying a sample in the amplified signal to be a heart beat point only when the sample value is equal to the first threshold signal and greater than the filtered threshold signal,
   wherein filtering the raw ECG data comprises:
   filtering the raw ECG data using a cascade of median filter and low pass filter;
   delaying the raw ECG data and
   subtracting an output signal of the low pass filter from the delayed raw ECG data in order to deliver a high pass filtered data.

2. The method of claim 1, further comprising:
   filtering the raw ECG data using a non-linear filter to minimize baseline wander of each PQRST pattern to form a viewable ECG signal; and
   annotating the viewable ECG signal to indicate each heart beat point.

3. The method of claim 2, wherein filtering the raw ECG data comprises:
   filtering the raw ECG data using a cascade of median filter and low pass filter;
   delaying the raw ECG data; and
   subtracting an output signal of the low pass filter from the delayed raw ECG data in order to deliver a high pass filtered data.

4. The method of claim 1, wherein the amplified signal is formed by squaring the filtered ECG data at least one time.

5. The method of claim 1, wherein filtering the third threshold signal comprises:
   filtering the third threshold signal with a first order infinite impulse response (IIR) filter; and
   dynamically selecting a cutoff frequency for the IIR as a linear function of a difference between a logarithm of the first threshold signal and a logarithm of the second threshold signal.

6. The method of claim 1, wherein filtering the third threshold signal comprises:
   filtering the third threshold signal with a first order infinite impulse response (IIR) filter; and
   dynamically selecting a cutoff frequency for the IIR as a linear function of a ratio of the first threshold signal and the second threshold signal.

7. The method of claim 1, wherein deriving a first threshold signal and a third threshold signal using a moving max filter on the amplified signal uses a first window width for the first threshold signal and a different window width for the third threshold signal.

8. A computer-readable non-transitory storage media having computer-readable instructions stored therein that when executed by a computer performs a method of processing ECG data in real time, the method comprising:
   receiving a stream of raw ECG data samples comprising PQRST patterns from an analog front end coupled to the computer;
   filtering the raw ECG data to form filtered ECG data by using a non-linear filter to minimize baseline wander and to suppress a T wave portion of each PQRST pattern;
   performing a non-linear operation on the filtered ECG data to form an amplified signal that exaggerates an R peak of each PQRST pattern;
   deriving a first threshold signal and a third threshold signal using a moving max filter on the amplified signal;
   deriving a second threshold signal using a moving average filter on the amplified signal;
   filtering the third threshold signal to form a filtered threshold signal using a filter in which a cutoff frequency is dynamically selected as a function of the first threshold signal and the second threshold signal; and
   identifying a sample in the amplified signal to be a heart beat point only when the sample value is equal to the first threshold signal and greater than the filtered threshold signal,
   wherein filtering the raw ECG data comprises:
   filtering the raw ECG data using a cascade of median filter and low pass filter;
   delaying the raw ECG data; and
   subtracting an output signal of the low pass filter from the delayed raw ECG data in order to deliver a high pass filtered data.

9. The computer-readable non-transitory storage media of claim 8, further comprising:
   filtering the raw ECG data using a non-linear filter to minimize baseline wander of each PQRST pattern to form a viewable ECG signal;
   annotating the viewable ECG signal to indicate each heart beat point; and
   displaying the annotated viewable ECG signal on a display coupled to computer.

10. The computer-readable non-transitory storage media of claim 8, wherein the amplified signal is formed by squaring the filtered ECG data at least one time.

11. The computer-readable non-transitory storage media of claim 8, wherein filtering the third threshold signal comprises:
    filtering the third threshold signal with a first order infinite impulse response (IIR) filter; and dynamically selecting a cutoff frequency for the IIR as a linear function of a difference between a logarithm of the first threshold signal and a logarithm of the second threshold signal.

12. The computer-readable non-transitory storage media of claim 8, wherein filtering the third threshold signal comprises:
    filtering the third threshold signal with a first order infinite impulse response (IIR) filter; and
    dynamically selecting a cutoff frequency for the IIR as a linear function of a ratio of the first threshold signal and the second threshold signal.

13. The computer readable non-transitory storage media of claim 8, wherein the computer readable storage media is comprised within a smart phone.

14. The computer readable non-transitory storage media of claim 8, wherein the computer readable storage media is comprised within a medical system.

\* \* \* \* \*